(12) United States Patent
Avramescu et al.

(10) Patent No.: US 9,097,638 B2
(45) Date of Patent: Aug. 4, 2015

(54) SENSING DEVICES AND METHODS

(75) Inventors: Viorel Avramescu, Bucharest (RO);
Cazimir G. Bostan, Bucharest (RO);
Ion Georgescu, Bucharest (RO)

(73) Assignee: Honeywell International Inc.,
Morristown, NJ (US)

( * ) Notice: Subject to any disclaimer, the term of this patent is extended or adjusted under 35 U.S.C. 154(b) by 457 days.

(21) Appl. No.: 13/208,107

(22) Filed: Aug. 11, 2011

(65) Prior Publication Data

US 2012/0036917 A1 Feb. 16, 2012

(30) Foreign Application Priority Data

Aug. 11, 2010 (EP) ..................... 10172492

(51) Int. Cl.
*G01N 7/00* (2006.01)
*G01N 29/02* (2006.01)
*G01N 29/24* (2006.01)
*G01N 29/30* (2006.01)

(52) U.S. Cl.
CPC .......... *G01N 29/022* (2013.01); *G01N 29/2481* (2013.01); *G01N 29/30* (2013.01); *G01N 2291/02845* (2013.01); *G01N 2291/02881* (2013.01); *G01N 2291/0423* (2013.01); *G01N 2291/106* (2013.01); *Y10T 29/42* (2015.01)

(58) Field of Classification Search
CPC ..................................................... G01N 25/56
See application file for complete search history.

(56) References Cited

U.S. PATENT DOCUMENTS

| 4,879,487 | A | * | 11/1989 | Sugai et al. ............. 333/193 |
| 5,571,944 | A | | 11/1996 | Pfeifer et al. |
| 2003/0009270 | A1 | * | 1/2003 | Breed ...................... 340/438 |
| 2009/0193903 | A1 | | 8/2009 | Cobianu et al. |
| 2010/0058857 | A1 | | 3/2010 | Zhang |
| 2010/0127834 | A1 | | 5/2010 | Cobianu et al. |
| 2010/0141087 | A1 | | 6/2010 | Bostan |

OTHER PUBLICATIONS

Search Report from related European Application No. 10172492.0-1554, dated May 5, 2013, 5 pgs.
Bill Drafts "Acoustic Wave Technology Sensors", IEEE Transactions on Microwave Theory and Techniques, IEEE Service Center, vol. 49, No. 4, Apr. 1, 2001, 8 pgs. (XP011038300).
Search Report from related European Application No. 10172492.0-1554, dated Jan. 5, 2011, 3 pgs.

(Continued)

*Primary Examiner* — Laura Martin
*Assistant Examiner* — Alex Devito
(74) *Attorney, Agent, or Firm* — Brooks, Cameron & Huebsch, PLLC (57) ABSTRACT

Embodiments of the present disclosure include devices and methods for humidity and temperature sensing. For example, in one embodiment, a sensing device can include a first surface acoustic wave (SAW) component, wherein the first SAW component is a temperature component, a second SAW component, wherein the second SAW component is a humidity component, a third SAW component, wherein the third SAW component is a reference component, and a piezoelectric layer, wherein the first SAW component, the second SAW component, and the third SAW component are on a surface of the piezoelectric layer.

9 Claims, 6 Drawing Sheets (56) References Cited

OTHER PUBLICATIONS

Avramescu, et al. "Surface Acoustic Wave devices and their sensing capabilites", Semiconductor Conference, 2009, Oct. 12, 2009, 10 pgs. (XP 031569033).

Avramescu, V., et al. "Surface Acoustic Wave Devices and Their Sensing Capabilities," Semiconductor Conference, Oct. 12, 2009. pp. 27-36. IEEE Service Center, Piscataway, NJ, US.

Drafts, Bill. "Acoustic Wave Technology Sensors," IEEE Transactions on Microwave Theory and Techniques, Apr. 1, 2001. pp. 795-802, vol. 49, No. 4. IEEE Service Center, Piscataway, NJ, US.

European Search Report for related European Patent Application No. 10172492.0 dated Jan. 5, 2011 (3 pages).

Communication pursuant to Article 94(3) EPC for related European Patent Application No. 10172492.0 dated Jan. 21, 2011 (5 pages).

\* cited by examiner

SENSING DEVICES AND METHODS

PRIORITY INFORMATION

This application claims priority to European Patent Application Serial No. 10172492.0, filed Aug. 11, 2010, the specification of which is incorporated by reference herein.

BACKGROUND

The present disclosure is related generally to the field of sensing devices. More particularly, the present disclosure is related to humidity and temperature sensing devices.

Sensing devices can use a number of methods to sense phenomena that can be correlated to a desired measurement. One sensing method uses interdigitated transducers (IDTs) to convert electrical energy to mechanical energy and to convert mechanical energy to electrical energy.

The IDTs can use the mechanical energy and/or electrical energy to correlate phenomena associated with either type of energy to a characteristic. An IDT can be placed on the surface of an object and transform mechanical energy from the object to electrical energy. An IDT on the surface of an object can also transform electrical energy supplied to the IDT into mechanical energy that can be transferred to the object on which the IDT is placed.

An IDT can be included in a resonator that includes an IDT and a series of reflectors that reflect mechanical energy back to the IDT. Phenomena associated with the mechanical energy, such as the velocity of the surface waves, can be sensed and measured by the IDT. In some arrangements, the mechanical energy can be transformed back into electrical energy by the IDT.

An IDT can be included in a delay line. A delay line can include a first IDT that generates mechanical energy from electrical energy and a second IDT that receives the mechanical energy generated by the first IDT. In such embodiments, phenomena associated with the mechanical energy, such as the velocity of the surface waves, can be sensed and measured by the second IDT. The mechanical energy received by the second IDT can be transformed back into electrical energy by the second IDT.

Resonators and delay lines can use the phenomena sensed by the IDTs and correlate it to a desired measurement characteristic. Resonators and delay lines can be used to correlate phenomena associated with electrical and/or mechanical energy sensed by IDTs to measurements, such as temperature, mass loading, and/or strain/stress, among other measurements.

Sensing devices using IDTs can be limited by in their ability to measure phenomena with sufficient resolution and to transmit the measurements from the sensing devices in certain environments. Additionally, the cost, amount of time, and/or difficulty associated with manufacturing IDT based sensing devices can be high, which may not be suitable for some applications.

DETAILED DESCRIPTION

Embodiments of the present disclosure include devices and methods for humidity and temperature sensing. For example, in some embodiments, a sensing device can include a first surface acoustic wave (SAW) component, wherein the first SAW component is a temperature component, a second SAW component, wherein the second SAW component is a humidity component, a third SAW component, wherein the third SAW component is a reference component, and a piezoelectric layer, wherein the first SAW component, the second SAW component, and the third SAW component are on a surface of the piezoelectric layer.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and/or structural changes may be made without departing from the scope of the present disclosure.

Figure 1A:
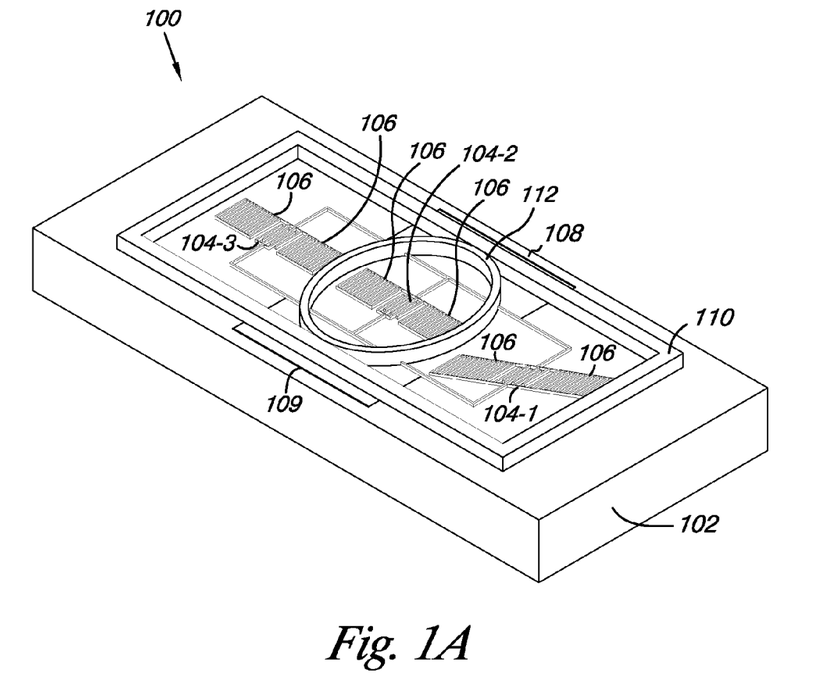
FIGS. 1A-1B illustrate an embodiment of the present disclosure that includes a sensing device having surface acoustic wave (SAW) components.
Figure 1B:
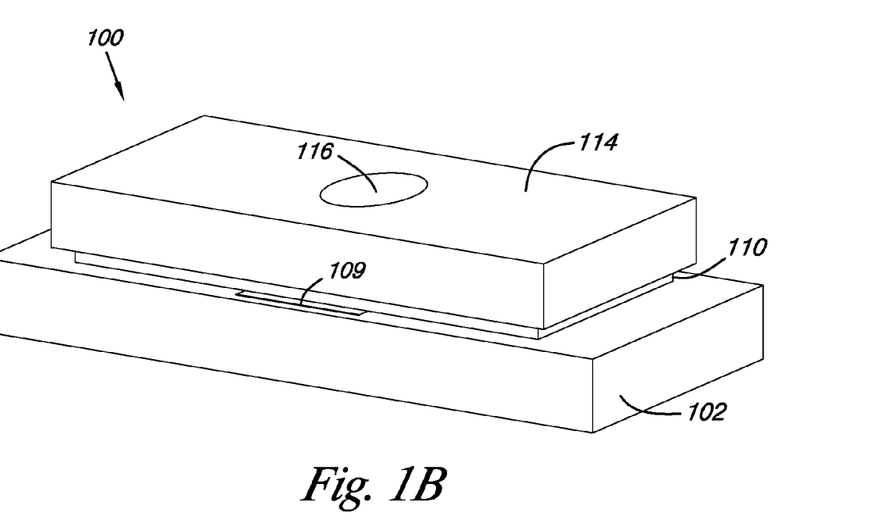

FIGS. 1A-1B illustrate an embodiment of the present disclosure that includes a sensing device having surface acoustic wave (SAW) components. In FIG. 1A, sensing device 100 includes a number of SAW components 104-1, 104-2, and 104-3.

The SAW components 104-1, 104-2, and 104-3 are resonators in FIG. 1A. A resonator can include a resonant cavity with an interdigitated transducer (DT) and a series of reflectors 106.

Each of the SAW components 104-1, 104-2, and 104-3 in FIG. 1A are resonators that include an IDT and a series of reflectors 106. The reflectors 106 can reflect waves to keep the waves inside the resonator.

The SAW components 104-1, 104-2, and 104-3 and reflectors 106 for each SAW component are on a piezoelectric layer 102. In some embodiments, the piezoelectric layer 102 can be quartz, among other piezoelectric materials.

The piezoelectric layer 102 can be the layer where waves, such as surface acoustic waves, are generated by the SAW components 104-1, 104-2, and 104-3 for the sensing device 100. The waves on the surface of the piezoelectric layer 102 can be affected by the temperature, humidity, and/or conductivity, among other factors, of the area surrounding the sensing device 100 and/or the piezoelectric layer itself.

The IDT of each SAW component 104-1, 104-2, and 104-3 can generate mechanical waves on the surface of the piezoelectric layer 102. The velocities of the waves on the surface of the piezoelectric layer sensed and transformed in frequency variations of an electrical signal by the IDTs that are used to determine the temperature and humidity near the sensing device 100. The waves on the surface of the piezoelectric layer sensed by the IDTs can be Rayleigh waves and/or pseudo-SAW waves, such as leaky waves, surface trapped waves, and/or guided waves, among other types of waves.

SAW component 104-1 is positioned on the piezoelectric layer 102 at a different angle in relation to SAW components 104-2 and 104-3. This offset can be used to account for the effects of factors, such as temperature, stress, and other factors, on the measurements taken by the sensing device 100.

The sensing device 100 can include electrical connections 108 and 109. The electrical connections 108 and 109 can be coupled to the IDTs of each of the SAW components 104-1, 104-2, and 104-3.

The electrical connections 108 and 109 can be formed on the surface of the piezoelectric layer 102. The electrical connections 108 and 109 can be coupled to an antenna and/or an interrogator to facilitate the transfer of signals that include frequency data from the SAW components 104-1, 104-2, and 104-3.

The sensing device 100 can include barriers 110 and 112. Barriers 110 and 112 can be used to isolate and seal the SAW components 104-1, 104-2, and 104-3 from each other and the surrounding environment when used with a cover, described below in association with FIG. 1B.

Barriers 110 and 112 can be made of glass frit, photo-printable polymers, and/or other suitable materials to seal the various portions of the sensing device 100 having the SAW components 104-1, 104-2, and 104-3 from each other. The barriers 110 and 112 can be formed on the piezoelectric layer 102 and over the electrical connections 108 and 109. The barriers 110 and 112 cannot be made of a conductive material so they would not interfere with the transfer of signals from the SAW components 104-1, 104-2, and 104-3 to an antenna and/or interrogator through the electrical connections 108 and 109.

In one or more embodiments, the SAW components can be in delay line configurations. A delay line configuration includes two IDTs.

In some such embodiments, a first IDT is used to generate waves on the surface of the piezoelectric layer and a second IDT can be used to capture the waves on the surface of the piezoelectric layer generated by the first IDT. In a delay line configuration, the waves captured by the second IDT are only the waves generated by the first IDT that propagate in the direction from the first to the second IDT.

In a SAW component having a resonator, the waves captured by the IDT are dependent on the effectiveness of the reflectors to reflect the waves generated by the IDT back to the IDT. In a resonator SAW device, the waves reflected by the reflectors back to the IDT are captured.

In FIG. 1B, the sensing device 100 of FIG. 1A is illustrated with a cover 114 placed over the piezoelectric layer 102 and on the barriers. The cover 114 can be made of the same material as the piezoelectric layer 102. This can reduce stress caused by temperature between the cover 114 and the piezoelectric layer 102.

The cover 114 can include an opening 116. For example, opening 116 can expose SAW component 104-2 to the environment surrounding the sensing device 102, while the cover 114 and the barriers 110 and 112 combine to prevent SAW components 104-1 and 104-3 from being exposed to the environment surrounding the sensing device 102.

In some embodiments, barriers can be coupled to both the piezoelectric layer 102 and the cover 114. In such embodiments, the barriers are formed on the piezoelectric layer 102. They can, for example, be formed of glass frit and/or photo-printable polymers. In some embodiments, the barriers can be part of the cover 114.

In one or more embodiments, SAW components 104-1, 104-2, and 104-3 can be used to measure the temperature and humidity of the area near the sensing device 100. The SAW components 104-1, 104-2, and 104-3 can be used to convert the variations of the velocity of the waves on the surface of the piezoelectric layer 102 to variations of the frequency of an electrical signal and determine the frequency of those electrical signals. The frequency of the electrical signals provided by the SAW components 104-1, 104-2, and 104-3 can be used to determine temperature and humidity of the area near the sensing device by correlating the frequencies to temperature and humidity.

The sensing device 102 operates by having the SAW components 104-1, 104-2, and 104-3 convert electrical energy to mechanical energy to create waves, such as surface acoustic waves, on the surface of the piezoelectric layer 102. The waves are then captured by the SAW components 104-1, 104-2, and 104-3 and their energy is transformed back into the energy of an electrical signal that has specific frequencies determined by the design of the SAW components 104-1, 104-2, and 104-3 and by the velocity of the surface waves.

The frequency of the electrical signal obtained in the aforementioned way can be affected by the temperature of the piezoelectric layer 102 and the environment surrounding the sensing device. The frequency can also be affected by factors such as the conductivity of the piezoelectric layer 102 and the humidity of the environment surrounding the sensing device 100.

The humidity of the environment surrounding the sensing device 100 can, for example, affect the frequency of the waves on the piezoelectric layer due to the moisture by humidity adsorption on the surface of the piezoelectric material, which is related to the humidity of the environment surrounding the sensing device. The amount of moisture on the surface of the piezoelectric layer 102 can change the mass of the surface of the piezoelectric layer 102 and changes in the mass of the surface of the piezoelectric layer 102 can increase or decrease the velocity of the waves on the surface of the piezoelectric layer 102. This leads to modification of the frequency associated electrical signal. Accordingly, changes in the humidity of the environment surrounding the sensing device 100 change the velocity of the waves on the surface of the piezoelectric layer 102 by changing the mass of the surface of the piezoelectric layer 102.

In some embodiments, SAW component 104-3 can be a reference SAW component. In such embodiments, the reference SAW component can have a resonant frequency that can be used to eliminate and/or reduce the effects of surface stress and other unwanted effects on the piezoelectric layer 102 when determining the temperature and humidity of the environment surrounding the sensing device 100.

SAW component 104-2 can be a humidity SAW component. For example, the humidity SAW component can have a resonant frequency that can be used to determine the humidity of the environment surrounding the sensing device 100. The SAW component 104-2 can be used as a humidity SAW component, for instance, because it is exposed to the environment surrounding the sensing device 100 via opening 116.

In some embodiments, the SAW component 104-1 can be a temperature SAW component. This SAW component 104-1 can have a resonant frequency that has a different temperature behavior due to the fact it is angled with respect to the other two SAW components, 104-2 and 104-3. Thus, by subtracting the frequency of the SAW reference component 104-3 from the frequency of the SAW temperature component 104-1 the result depends only on temperature. For example, the temperature SAW component can have a resonant frequency that is used to determine the temperature of the environment surrounding the sensing device 100. A temperature SAW component and a reference SAW component can be sealed from the environment surrounding the sensing device 100. Accordingly, these components are unaffected by the humidity of the environment surrounding the sensing device 100.

In one or more embodiments, the reference frequency, the temperature frequency, and the humidity frequency are used in the determination of the temperature and humidity of the area near the sensing device 100. In such embodiments, the reference frequency can, for example, be subtracted from the temperature frequency to obtain a normalized temperature frequency and the reference frequency can be subtracted from the humidity frequency to obtain a normalized humidity frequency.

The normalized temperature frequencies can be correlated to temperatures through experimental data. Normalized humidity frequencies can be correlated to the humidity through experimental data. Humidity is also a function of temperature, therefore, the normalized temperature frequencies can be used when correlating the measured frequencies to humidity.

In one or more embodiments, the SAW components can be calibrated to operate in a frequency range that correlates to the temperature and humidity of a desired operating range for the sensing device 100. Also, in some embodiments, the SAW components can be calibrated to operate in the industrial scientific medical (ISM) frequency band.

The resonant frequencies are typically different for each of the SAW components. Therefore, the frequencies obtained by an interrogator from the SAW components can be differentiated by the interrogator as to their respective type, e.g., reference frequency, temperature frequency, and humidity frequency.

Figure 2A:
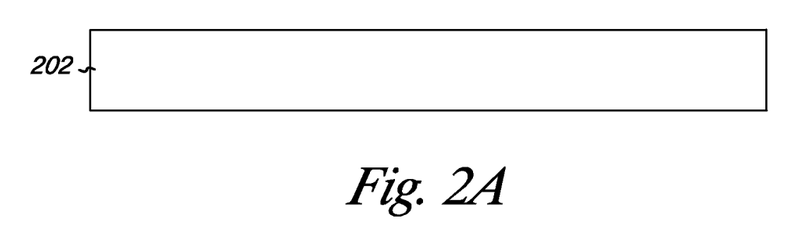
FIGS. 2A-2E illustrate a process associated with forming a sensing device in accordance with embodiments of the present disclosure.

FIGS. 2A-2E illustrate a process associated with forming a sensing device in accordance with embodiments of the present disclosure. FIG. 2A illustrates a piezoelectric layer 202 being formed.

The piezoelectric layer 202 can be made of any piezoelectric material, such as quartz. The piezoelectric layer 202 can act as the substrate for the sensing device and each of the other elements of the sensing device can be built on and/or over the piezoelectric layer 202.

Figure 2B:
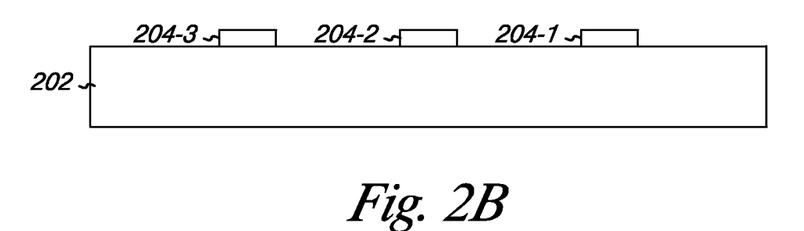

In FIG. 2B, the SAW components 204-1, 204-2, and 204-3 are formed on the piezoelectric layer 202. The SAW components 204-1, 204-2, and 204-3 can be formed, for example, by patterning a metal on the piezoelectric layer to form an IDT and/or reflectors. The SAW components 204-1, 204-2, and 204-3 can be formed by using physical vapor deposition (PVD), among other suitable deposition techniques.

In some embodiments, the SAW component 204-1, 204-2, and 204-3 formation can include forming the IDT and reflectors for each SAW component in a resonator configuration. In some embodiments, the SAW component 204-1, 204-2, and 204-3 formation can include forming the IDTs for each SAW component in a delay line configuration.

The electrical connections can, for example, be formed on a surface of the piezoelectric layer 202 and can be coupled to each of the SAW components 204-1, 204-2, and 204-3. The electrical connections can be formed, for instance, by patterning metal on the surface of the piezoelectric layer 202.

Figure 2C:
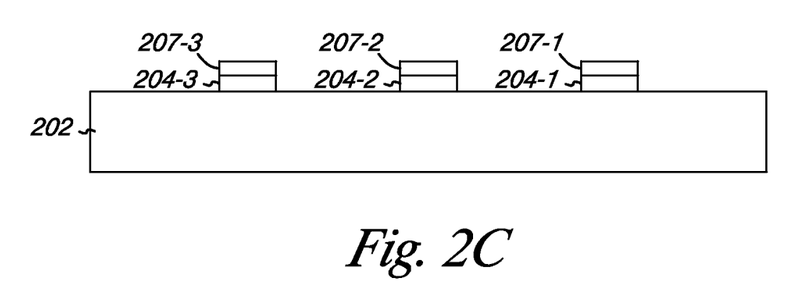

In FIG. 2C, a layer of silicon dioxide ($SiO_2$) is formed on a portion, including the IDT, of the SAW components 204-1, 204-2, and 204-3. In the embodiment of FIG. 2C, $SiO_2$ layer 207-1 is formed on a portion of SAW component 204-1, $SiO_2$ layer 207-2 is formed on a portion of SAW component 204-2, and $SiO_2$ layer 207-3 is formed on a portion of SAW component 204-3.

The $SiO_2$ layers can have a thickness of, for example, approximately 20 nanometers (nm) and can be hygroscopic.

The $SiO_2$ layers 207-1, 207-2, and 207-3 can be formed using plasma enhanced chemical vapor deposition (PECVD), among other deposition methods. The $SiO_2$ layers 207-1, 207-2, and 207-3 can increase the SAW components sensitivity to humidity. For example, a $SiO_2$ layer of approximately 20 nm can cause a SAW component to have a frequency to percent humidity sensitivity of approximately a 0.8 kHz change in frequency that correlates to approximately a 1% change in humidity. The SAW components sensitivity to humidity can be increased by using a thicker layer of $SiO_2$ and can be decreased by using a thinner layer of $SiO_2$.

Figure 2D:
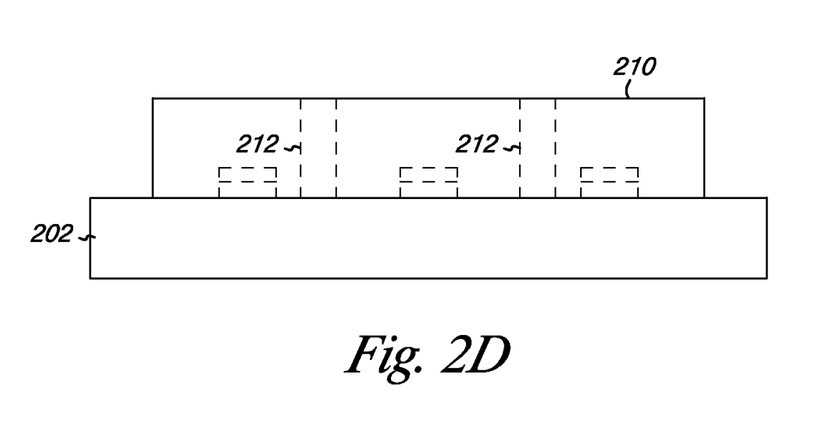

In FIG. 2D, barrier 210 and barrier 212 are formed on the piezoelectric layer 202. The barriers can, for example, be made of glass frit and/or photo-printable polymers. The barriers can be formed on the piezoelectric layer by any suitable method, as long as the method does not interfere with the electrical connections between the SAW components and an antenna and/or interrogator.

Figure 2E:
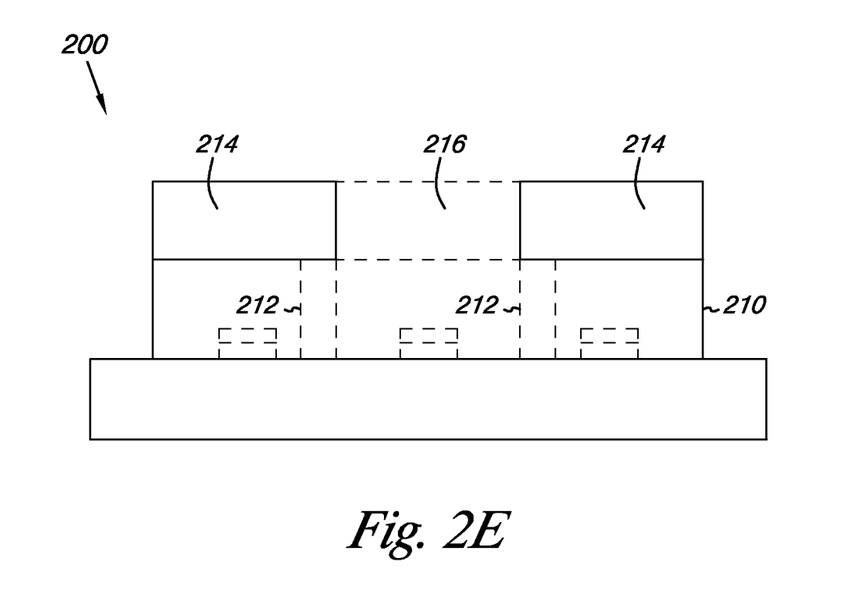

In FIG. 2E, sensing device 200 includes a cover 214 that is coupled to the barriers. The cover 214 can be made of the same material as the piezoelectric layer 202. This can be beneficial, for example, to reduce thermal stress on the surface of the piezoelectric layer that could be caused by forming with materials with differing thermal properties.

Prior to coupling the cover 214 to the barriers, an opening 216 can be formed in cover 214. Opening 216 can be formed, for example, by using a suitable technique such as wet etching, ultrasonic milling, sand blasting, and/or laser milling, among other techniques. Opening 216 can be formed at a location in the cover 214 so that the barrier surrounding the humidity SAW component approximately aligns with the perimeter of opening 216 when the cover 214 is coupled to the barriers.

When cover 214 is coupled to the barriers it causes the reference SAW component and the temperature SAW component to be sealed from the environment surrounding the sensing device 200. The opening 216 in cover 214 allows for the humidity SAW component to be exposed to the environment surrounding the sensing device 200.

Figure 3:
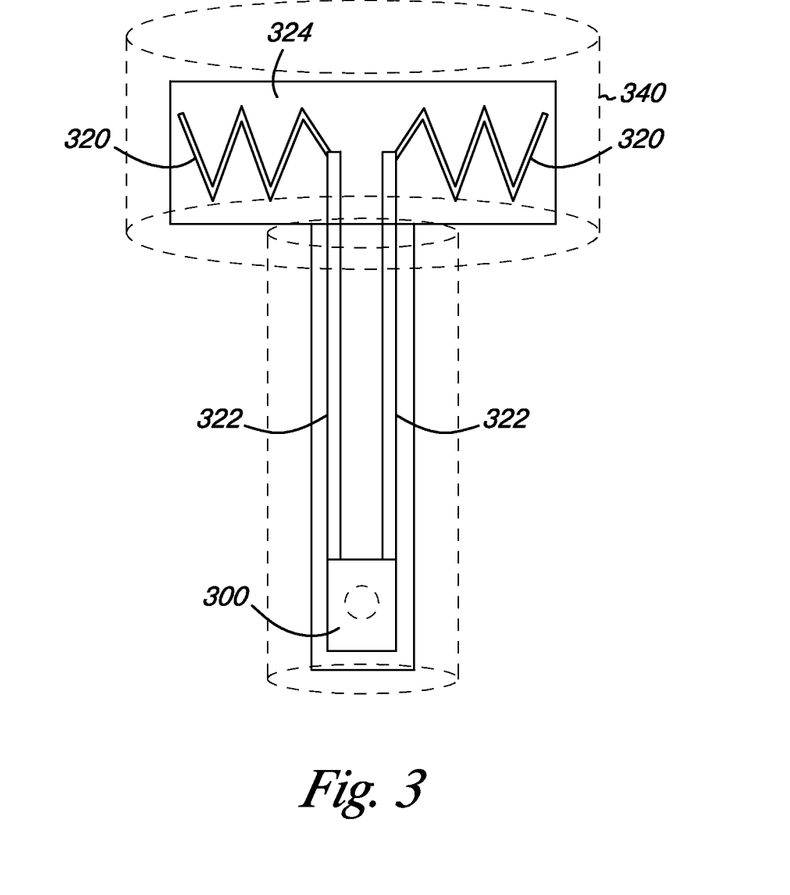
FIG. 3 illustrates an embodiment of the present disclosure that includes a sensing device assembly having an antenna and SAW components.

FIG. 3 illustrates an embodiment of the present disclosure that includes a sensing device assembly having an antenna and SAW components. In FIG. 3, a sensing device assembly 340 includes a sensing device 300 and a printed circuit board (PCB) 324 with transmission lines 322, and an antenna 320. The transmission lines 322 can be coupled between the antenna 320 and the electrical connections of the sensing device 300.

In one or more embodiments, antenna 320 can include a wireless transducer. In the embodiment illustrated in FIG. 3, the antenna 320 with a wireless transducer operates without a power supply.

In such an embodiment, the transducer gathers power from the electromagnetic waves that are sent from the interrogator to interrogate the sensor. The power gathered by the transducer in the antenna can be used to provide electrical energy to the SAW components which convert the electrical energy to mechanical energy by, for example, generating waves on the surface of the piezoelectric layer.

The velocity shift due to interaction of the waves with the surrounding medium is translated in a frequency shift of the SAW component. Thus, the mechanical energy of the waves can be converted back into electrical power. The electrical power generated by the SAW components from the mechanical energy of the waves can be used to transmit the signals that indicate the frequency data for the waves on the surface of the piezoelectric layer from the antenna to the interrogator. This configuration allows the sensing device assembly 340 to operate without a power supply, thus reducing the maintenance costs associated with the using the sensing device of the present disclosure, in some instances.

In one or more embodiments, a sensing device assembly can include an interrogator that is coupled directly to the sensing device. In such embodiments, an antenna is not needed as the signals from the SAW components are sent to the interrogator via the coupling mechanism between the sensing device and the interrogator.

Figure 4:
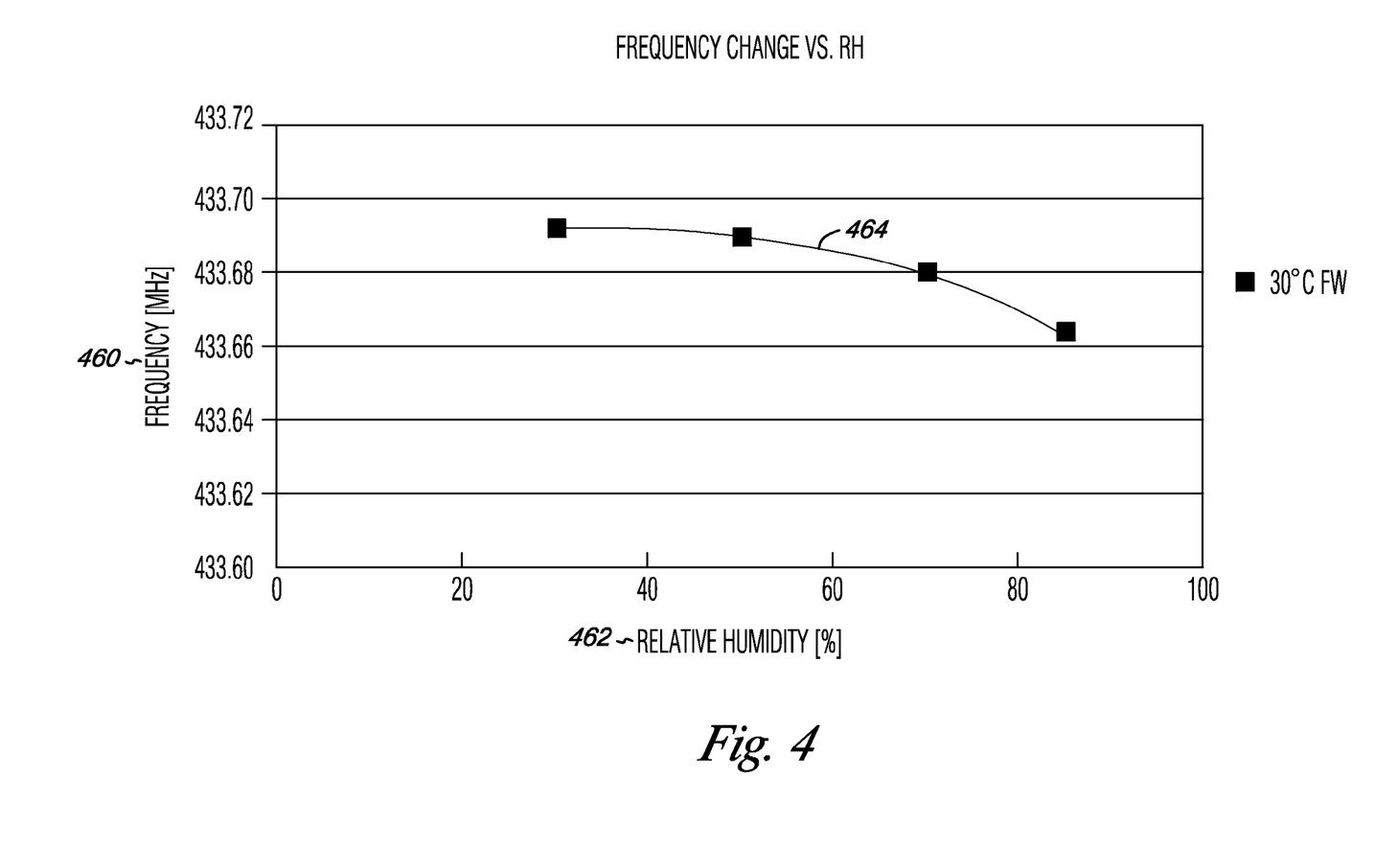
FIG. 4 is a graph illustrating the relationship between the resonant frequency of the humidity SAW component and the relative humidity of the environment surrounding the sensing device according to an embodiment of the present disclosure.

FIG. 4 is a graph illustrating a relationship between the resonant frequency of the humidity SAW component and a relative humidity of the environment surrounding a sensing device according to an embodiment of the present disclosure. In FIG. 4, the resonant frequency of the SAW humidity component 460 for a sensing device 464 are illustrated on the y-axis of the graph and the relative humidity 462 of the environment surrounding the sensing device 464 are illustrated on the x-axis of the graph. The normalized humidity frequencies 460 are illustrated in mega-hertz (MHz) and include the measured frequency of the reference SAW component subtracted from the measured frequency of the humidity SAW component.

In FIG. 4, as the relative humidity 462 increases, the resonant frequency of the SAW humidity component 460 decrease. This is because, as the humidity increases in the environment surrounding the sensing device, more moisture forms on the surface of the piezoelectric layer which increases the mass of the surface of the piezoelectric layer. The velocity of the waves generated on the surface of the piezoelectric layer decrease when the mass of the surface of the piezoelectric layer increases.

For example, in the embodiment, illustrated in FIG. 4, the resonant frequency of SAW humidity component has a value of 433.691 MHz for a relative humidity of 32% and decreases to 433.662 MHz for a relative humidity of 85%. In such an embodiment, the relationship between the resonant frequency of the SAW humidity component and relative humidity for the environment surrounding the sensing device 464 is not typically linear and the frequency tends to change in greater amounts for higher relative humidity's.

In one or more embodiments, the SAW components can be calibrated to operate at any desired frequency range for a desired temperature and/or humidity range. The frequency range for the SAW components can be within the ISM band and allow each SAW component to have a different resonant frequency.

Figure 5:
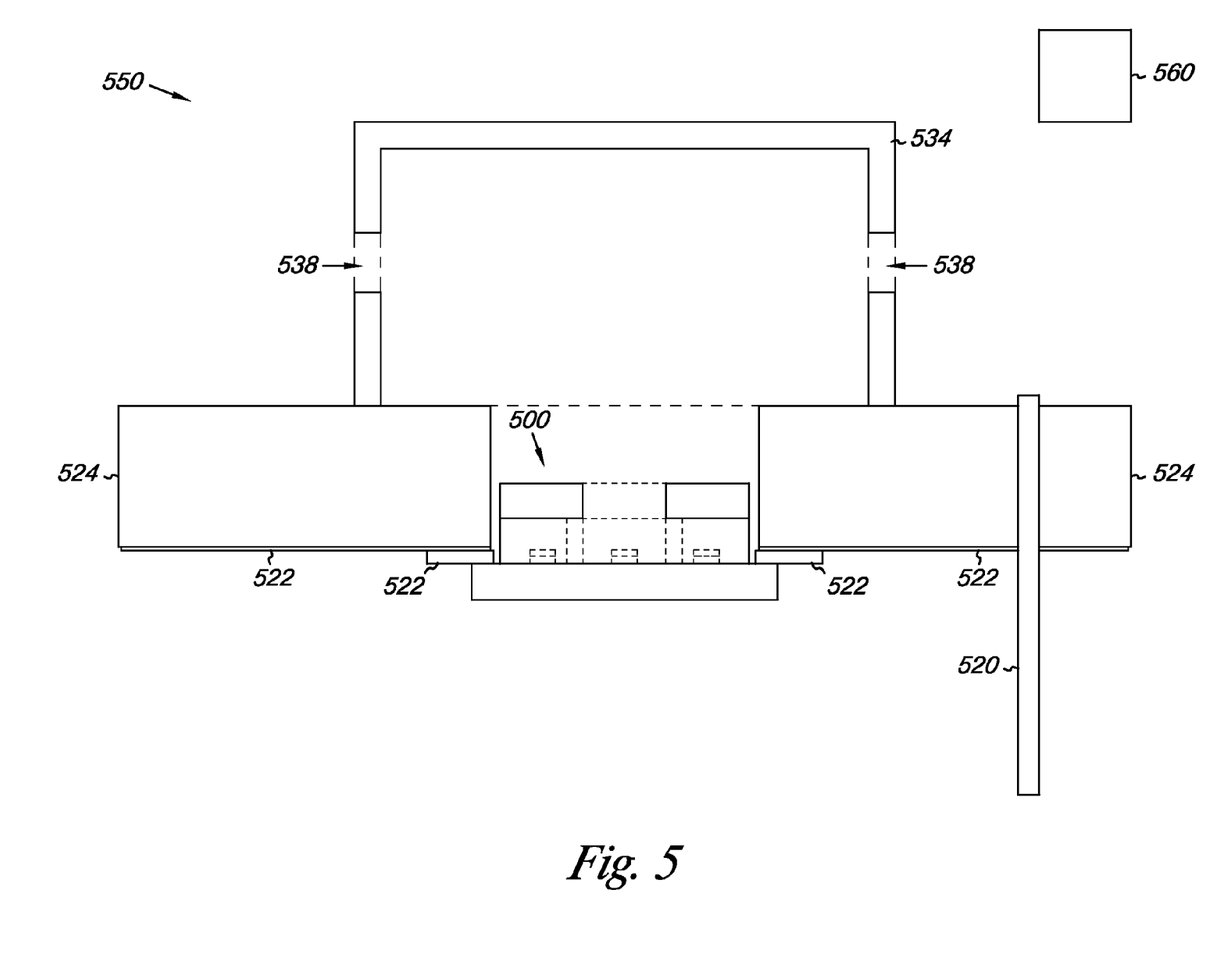
FIG. 5 illustrates an embodiment of the present disclosure that includes a sensing device assembly having components for attachment to the surface of an object.

FIG. 5 illustrates a view of an embodiment of the present disclosure that includes a sensing device assembly having components for attachment to the surface of an object. In FIG. 5, the sensing device assembly 550 includes a sensing device 500, a printed circuit board (PCB) 524, a cap 534, an antenna 520, and transmission lines 522.

The sensing device 500 is coupled to antenna 520 via transmission lines 522, which are on a PCB 524. Transmission lines 522 can include a conductive solder that is coupled to the electrical connections of the sensing device 500. The transmission lines 522 can also include a metal conductive path, such as copper, that electrically couples the conductive solder to antenna 520.

In FIG. 5, the sensing device assembly 550 includes a cap 534. The cap 534 can be made of plastic or any other suitable material. The cap 534 can be attached to an object, such as the wall of a tank, among other objects.

The cap 534 includes openings 538 to expose the sensing device 500 to the environment surrounding the sensing device. The cap 534 can be coupled to the PCB 524 of the sensing device assembly and the cap 534 can be glued to the surface of an object.

In FIG. 5, the frequency data of the waves on the surface of the piezoelectric layer from the SAW devices of the sensing device 500 can be sent to interrogator 560. Interrogator 560 can subtract the reference frequency from the temperature frequency to obtain a normalized temperature frequency and subtract the reference frequency from the humidity frequency to obtain a normalized humidity frequency. The normalized humidity and temperature frequencies can be correlated to the temperature and humidity by the interrogator 560.

In one or more embodiments, the sensing device assembly 550 does not need a power source. Therefore, the sensing device assembly 550 can be coupled to an object via cap 534 at locations that are not easily accessible because the sensing device assembly 550 does not have to be maintained in regular intervals, such as a device that requires a power supply.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

As used herein, the term "and/or" includes any and all combinations of one or more of the associated listed items. It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A sensing device, comprising:
a first surface acoustic wave (SAW) component, wherein the first SAW component is a temperature component and wherein silicon dioxide ($SiO_2$) is formed only on one surface of an interdigitated transducer (IDT) of the first SAW component;
a second SAW component, wherein the second SAW component is a humidity component and wherein silicon dioxide ($SiO_2$) is formed only on one surface of an interdigitated transducer (IDT) of the second SAW component;
a third SAW component, wherein the third SAW component is a temperature reference component and wherein silicon dioxide ($SiO_2$) is formed only on one surface of an interdigitated transducer (IDT) of the third SAW component; and
a piezoelectric layer, wherein the first SAW component, the second SAW component, and the third SAW component are on a surface of the piezoelectric layer.

2. The sensing device of claim 1, wherein the first SAW component, the second SAW component, and the third SAW component are resonators.

3. The sensing device of claim 1, wherein the first SAW component, the second SAW component, and the third SAW component are delay line components.

4. The sensing device of claim 1, wherein the second SAW component has a resonant frequency that is affected mainly by temperature and humidity.

5. The sensing device of claim 1, wherein the first SAW component has a resonant frequency that is affected mainly by temperature.

6. The sensing device of claim 1, wherein the first and third SAW components are sealed from the environment surrounding the sensing device and the second SAW component is exposed to the environment surrounding the sensing device.

7. The sensing device of claim 1, wherein the sensing device includes an antenna to transmit frequency data from the first, second, and third SAW components.

8. The sensing device of claim 1, wherein the piezoelectric layer is quartz.

9. The sensing device of claim 1, wherein the sensing device includes a cover coupled to the piezoelectric layer and the cover is made of the same material as the piezoelectric layer.

* * * * *